United States Patent [19]
Williams

[11] Patent Number: 5,154,711
[45] Date of Patent: Oct. 13, 1992

[54] OPHTHALMIC DEVICE

[76] Inventor: John Leslie Williams, 116 Banbury Road, Kidlington, Oxford OX5 2BX, England

[21] Appl. No.: 460,876
[22] PCT Filed: Jun. 5, 1989
[86] PCT No.: PCT/GB89/00620
   § 371 Date: Feb. 15, 1990
   § 102(e) Date: Feb. 15, 1990
[87] PCT Pub. No.: WO89/11840
   PCT Pub. Date: Dec. 14, 1989

[30] Foreign Application Priority Data
   Jun. 9, 1988 [GB] United Kingdom ............... 8813697
   Feb. 15, 1989 [GB] United Kingdom ............... 8903470

[51] Int. Cl.⁵ .............................................. A61F 9/00
[52] U.S. Cl. ................................................ 604/301
[58] Field of Search ................ 604/294, 300, 301, 302

[56] References Cited
U.S. PATENT DOCUMENTS

| | | | |
|---|---|---|---|
| 1,966,557 | 7/1934 | Michelson | 604/301 |
| 2,669,232 | 2/1954 | Borowick | 604/301 |
| 3,446,209 | 5/1969 | Macha | |
| 3,910,618 | 10/1975 | Massenz | |
| 4,531,944 | 7/1985 | Bechtle | |
| 4,543,096 | 9/1985 | Keene | |
| 4,733,802 | 3/1988 | Sheldon | |
| 4,740,206 | 4/1988 | Allander | 604/294 |

FOREIGN PATENT DOCUMENTS

0013187A1 9/1980 European Pat. Off.
1259476 3/1961 France.
1280014 7/1972 United Kingdom.

Primary Examiner—C. Fred Rosenbaum
Assistant Examiner—William W. Lewis
Attorney, Agent, or Firm—Davis, Bujold & Streck

[57] ABSTRACT

An ophthalmic device (10, 30, 50, 81) in the form of a cup (11, 31, 51) having a periphery (12, 32, 52, 85) substantially scaphoid in plan for contacting a facial region in the vicinity of an eye. The interior of the cup is accessible from its exterior by way of at least a first port (14, 34, 58, 86) and a second port (15, 35, 60, 87). The first port (14, 34, 58, 86) provides an inlet for a dispensing unit (17, 38, 63) for material to be supplied to the eye. The second port (15, 35, 60, 87) provides a target for viewing by an eye about which the periphery (12, 32, 52, 85) is disposed. The device (10, 30, 50, 81) is preferably fabricated from a material which is substantially opaque or imperfectly transparent and the second port (15, 35, 60, 87) is an aperture which provides a viewing target for an eye with which the device is being used. Alternatively the device can be in the form of a transparent shell with a distinctive target supported on the shell. A projection (16) can be located on the device (10, 30, 50, 81) outside the periphery (12, 32, 52, 85) to form an initial contact point for the device (10, 30, 50, 81) on a facial region in the vicinity of an eye. The projection (16) serves to enhance contact with, and displacement of, a displaceable surface in the region of the eye on which it is located on movement of the device (10, 30, 50, 81) relative to the eye.

8 Claims, 3 Drawing Sheets

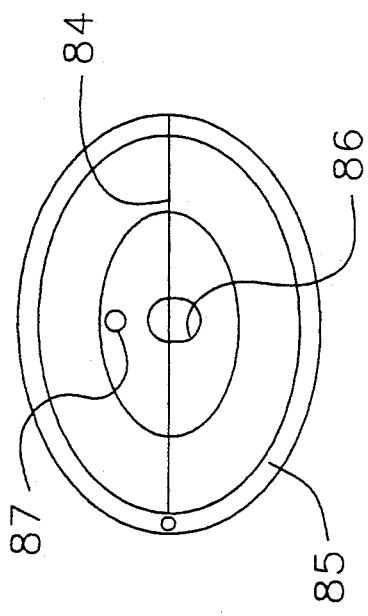
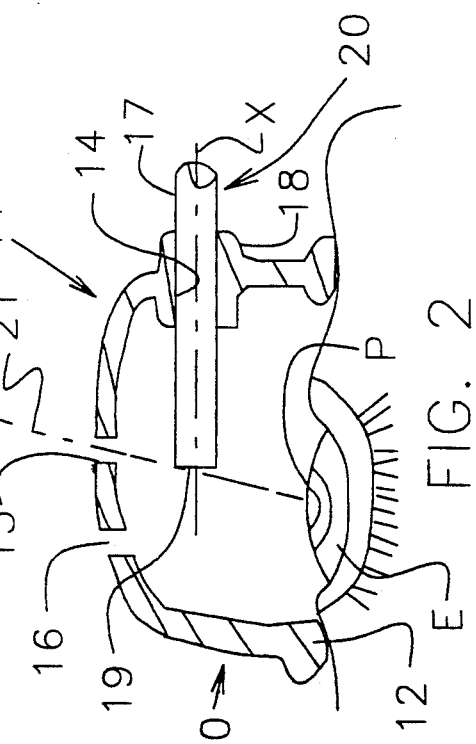
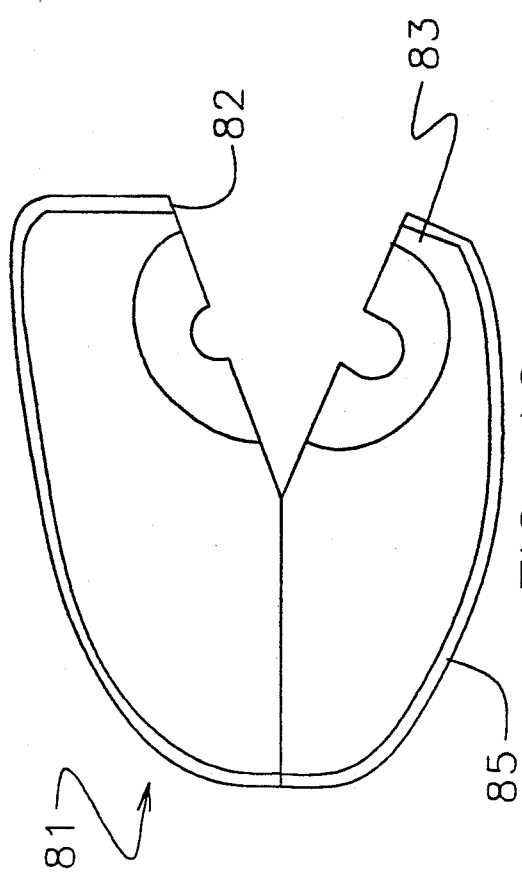
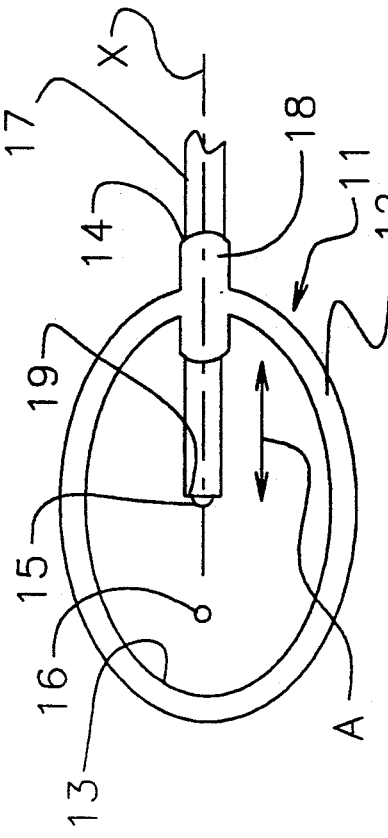

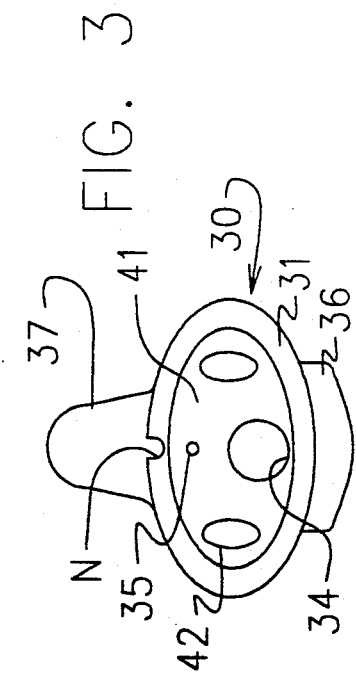
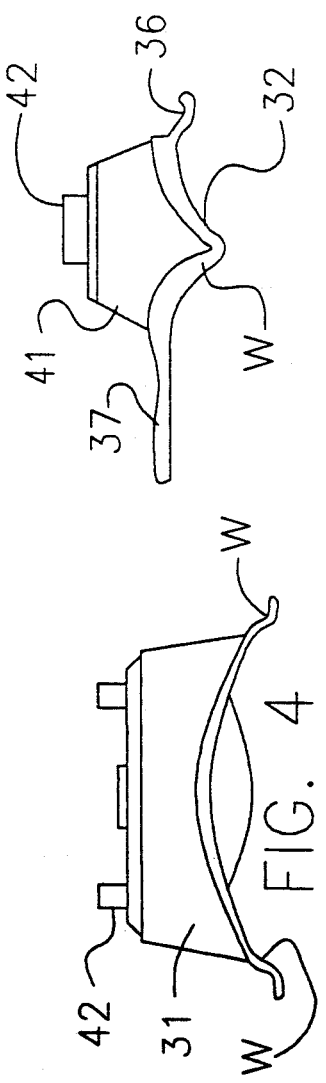
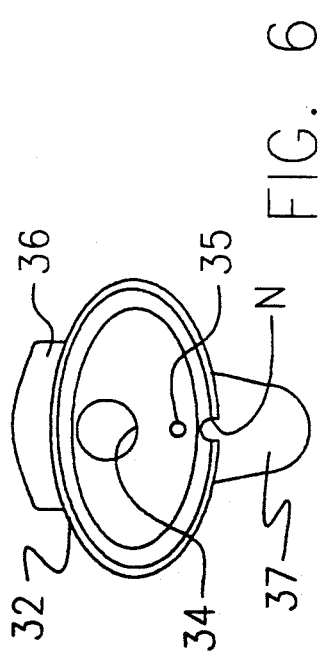
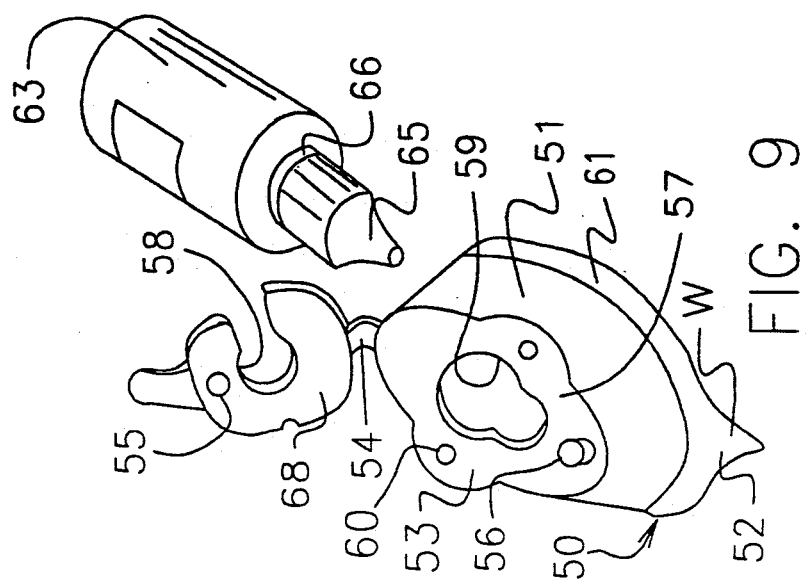

OPHTHALMIC DEVICE

This invention relates to an opthalmic device. It is particularly, though not exclusively, concerned with a device whereby a person can readily treat one of their own eyes with a material with reasonable efficiency. The material can be in virtually any material phase (such as a gas, vapor, liquid or powder).

A variety of methods are known for the treatment of eyes which require varying degrees of skill on the part of the user. A skilled practitioner can align the head of a patient and can use a simple dropper to administer the required number of drops of medication swiftly and on a part of the eye which ensures the most effective distribution to the eye. On many occasions it is necessary for patients to undertake self administration of eye treatment such as with drops or ointment. If the patient is a person wanting in self confidence or lacking manipulative skills attempts at self administration can result in ineffective application, if not total wastage, of medication.

For self administration of a liquid an alternative to an eyedropper is an eyebath whereby a liquid medication is carried to the eye so as to immerse at least a part of the eye. Thereafter the eye is opened and closed to provide for the distribution of medicament over the eye surface. This again requires a degree of manipulative skill and freedom of head action on the part of the user. In addition the method of application is necessarily a rather random affair involving the distribution of a relatively large amount of medication over a relatively large area despite a probable need for the medication to act on a relatively small area.

There is a need for an opthalmic device whose use results in the efficient application of medication to a selected area of the eye particularly for cases involving self administration According to a first aspect of the present invention there is provided an opthalmic device in the form of a cup having a periphery substantially scaphoid in plan for contacting a facial region in the vicinity of an eye; the cup interior being accessible from the exterior of the device by way of at least a first and a second port: the first port providing an inlet for a dispensing unit for material to be supplied to the eye, the second port providing a target for viewing by an eye about which the periphery is disposed.

According to a first preferred version of the first aspect of the present invention there is provided an opthalmic device fabricated from material which is substantially opaque or imperfectly transparent and the second port is an aperture whereby an eye with which the device is being used can see a distinct target area illuminated from outside the device.

According to a second preferred version of the first aspect of the present invention or the first preferred version thereof there is provided an opthalmic device incorporating a projection located on the device outside the periphery and adapted to form an initial contact point for the device on a facial region in the vicinity of an eye the projection serving to enhance contact with, and displacement of, a displacable surface in the region on which it is located on movement of the device relative to the eye.

According to a third preferred version of the first aspect of the present invention or the first and second preferred versions thereof there is provided an opthalmic device wherein a mounting is provided coupled to the remainder of the device by way of a hinge or other link, the mounting being adapted to locate a nozzle or other dispensing outlet of a dispenser retained in or by the mounting at a datum position relative to the mounting, the link enabling the mounting to be moved between: a first, working, position where the mounting, and a dispenser retained by the mounting, is in a dispensing position relative to the rest of the device; and a second, loading, position where the mounting is accessible to enable a dispenser to be secured to, or released from, the mounting so as to enable the mounting to be moved to the first position; the link further providing that the mounting in moving between the first and second positions causes the datum position to follow a path which does not contact the remainder of the device.

According to a fourth preferred version of the first aspect of the present invention or any preceding version thereof there is provided an opthalmic device wherein an aligning sight as a notch is provided on the device so that as the device is moved towards an eye, the aligning sight enables the eye to position the device relative to the eye at least immediately prior to contact between any part of the device and a region of the face in the vicinity of the eye.

According to a fifth preferred version of the first aspect of the present invention there is provided an opthalmic device wherein the cup is made up to two portions linked together by a hinge whereby the portions can be moved between a closed position wherein the device is available for use and an open position wherein a dispenser can be mounted in to or removed from the first port, the first port is defined by one or both portions.

According to a sixth preferred version of the first aspect of the present invention or any preferred version thereof there is provided an opthalmic device having a third port whereby the cup interior is accessible from its exterior, the third port providing a means for establishing a working position for a part of a dispensing unit when viewing, or when viewed by, an eye with which the device is used.

According to a seventh preferred version of the first aspect of the present invention or any preferred version thereof there is provided an opthalmic device composed entirely or substantially of a resilient deformable material to enable the cup in the course of use to be deformed from an initial undeformed state in which the interior of the cup is a first volume to a subsequent deformed state in which the interior of the cup is a second volume smaller than the first and thereafter released from its deformed state in the further course of use so as to enable the cup to restore itself to its initial undeformed state.

According to a second aspect of the present invention there is provided a eye treating device comprising an opthalmic device according to the first aspect of the present invention or any preferred version thereof together with a dispenser mounted in the first port to enable a nozzle or other dispensing outlet from the dispenser to be located in a datum position relative to the periphery of the device, the dispenser being operable from outside the cup to dispense material from the nozzle or other outlet into the cup interior.

Exemplary embodiments of the invention will now be described with reference to the accompanying drawings of opthalmic devices for dispensing medicament of which:

FIG. 1 is a rear view of a first embodiment; and

FIG. 2 is a horizontal cross-section on section II—II of FIG. 1.

FIG. 3 is a front view of a second embodiment;

FIG. 4 is an bottom view of the device shown in FIG. 3;

FIG. 5 is a side view of the device shown in FIG. 3; and

FIG. 6 is a view of the interior of the device shown in FIG.3.

FIG. 9 is a perspective view of a third embodiment;

FIGS. 12 and 13 are perspective views of a fourth embodiment shown respectively in an open and a closed position.

FIRST EMBODIMENT

FIGS. 1 and 2

Figure 7:
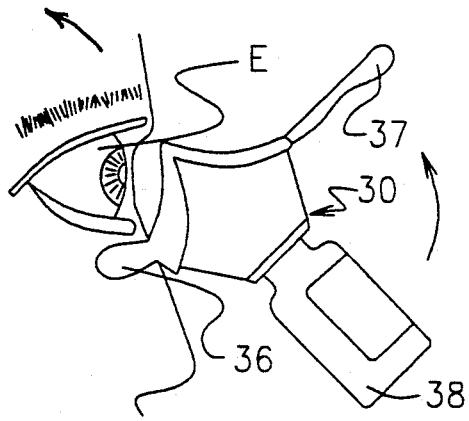
FIGS. 7 and 8 are perspective views (FIG. 8 being partially in section) of the device described in connection with FIGS. 3 to 6.
Figure 8:
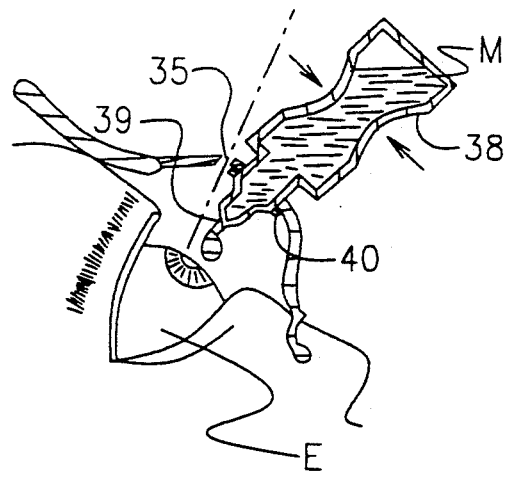

The device 10 is made up of a cup 11 of rubber having a thickened section forming a working periphery 12 which, as viewed in FIG. 1 is of scaphoid shape so as to be able to fit onto the face of a person in the vicinity of their eye. Wall 13 of the cup 11 is pierced by first port 14, second port 15 and third port 16.

First port 14 is adapted to receive a liquid dispenser 17 containing a medicament. The dispenser is retained by sleeve 18 integral with the cup 11. The dispenser 17 can be displaced back and forth in the direction of arrows A along axis X so that dispensing head 19 of the dispenser can be located at dispensing position 20 relative to eye E. Second port 15 and third port 16 provide for ambient light to be viewed by way of pupil P of eye E when the device is positioned eye as shown in FIG. 2. With the dispenser head off-set to the right from the position shown in FIG. 2 the path 21 from the pupil P to the second port 15 is unimpeded. However when dispenser head 19 is located at position 20 it intersects path 21 and obscures port 15 so indicating that the head 19 is correctly located.

Port 16 serves to provide a viewing target so that with device appropriately located to cover the eye when the eye E is directed to look at the port 16 it is correctly aligned to receive medicament ejected from dispenser head 19.

In use prior to locating the device 10 over the eye E the dispenser 17 is positioned within first port 14 with the dispensing head 19 positioned well to the right of path 21 as seen in FIG. 2. The cup 11 is then squeezed to reduce the interior volume of the cup which is then placed over the eye region as shown in FIG. 2 so that virtually the whole of the periphery 12 contacts skin surrounding the eye E. The cup 11 is then released and by virtue of its inherent resilience returns to its usual shape resulting in the skin around the eye being drawn back so exposing the eye ball more fully than is normally the case. In this position the pupil P can see ambient light by way of both the second port 15 and the third port 16. The dispenser 17 is then moved along axis X until dispensing head 19 intersects path 21 so effectively just obscuring port 15 from pupil P which thereafter is left with the third port 16 as the main or only visible target. Once the view from the pupil P is directed to this remaining target and with the head thrown back to position the eye substantially vertically beneath the dispenser outlet the dispenser 17 is operated to dispense the requisite amount of medicament. If necessary the head is turned to ensure that gravity acts in a direction ensuring that dispensed material is distributed appropriately into the region of the eye.

Once the dispensing operation is complete the device 10 is removed from the eye for cleansing and further usage.

If necessary the first port 14 can be adapted to receive a variety of dispensers appropriate for liquids, creams, powders, aerosols or whatever. However the relative cheapness of the device would enable discrete devices to be produced having a first port adapted for coupling with a specific dispenser opening or body section.

The described embodiment is intended for use in the self administration of eye medicament. It is particularly appropriate for use by a person who is diffident about self administration in the conventional manner which involves a fair degree of co-ordination involving hand and head attitude control and dispensing skill in a stressful situation.

Apart from self use the second and third ports allow the device to be used by an observer to view an eye covered by the device to ensure firstly that the dispenser is correctly positioned and secondly that the eye being treated is directed towards the third port at which time the observer causes the medicament to be dispensed. Typically such use can arise when treating a person incapable for whatever reason of treating themselves and in the treatment of animals. To facilitate use by an observer the second and third ports would be viewed by way of, for example, a fibre optic system allowing for both viewing and illumination of the eye under inspection.

SECOND EMBODIMENT

FIGS. 3 to 8

Device 30 comprises a cup 31 of plastics material having a working periphery 32 which, as variously viewed in FIGS. 3 to 6, is of scaphoid shape so as to be able to fit onto the face of a person around an eye. The cup has wing sections W on either side. Wall 33 of the cup 31 is pierced by first port 34 and second port 35. The cup has integral components comprising a lip 36 and an extension 37. An alignment notch N is provided on the upper part of the working periphery 32.

First port 34 is adapted to receive a liquid dispenser 38 (shown only in FIGS. 7 and 8) having a dispensing head 39 and containing a medicament M. The dispenser 38 is demountably retained by a resilient lip seal 40 integral with the cup 31.

The second port 35 serves as a viewing target so that with device appropriately located to cover the eye E when the eye E is directed to look at the port 35 it is correctly aligned to receive medicament M ejected from dispensing head 39 by squeezing the body of the dispenser 38.

The cup 31 has on its outer surface a flat section 41 carrying stubs 42 whereby a regulator (not shown) for the dispenser can be demountably secured to the device.

In use prior to locating the device over the eye E the dispenser 38 is mounted in first port 34 by way of the resilient seal 40. The device 30 is then moved towards the eye which views notch N so as to enable the device to be manipulated to ensure the correct alignment of the device relative to the eye. Eventually, as shown in FIG. 7, the lip 36 contacts the top of the cheek below the eye.

The device 30 is then moved on towards the eye so that wings W snugly fit around either end of the eye and beneath the eyebrow. In moving into position the device is moved downwardly so causing the lip 36 to move downwardly which causes the lower lid of the eye to be drawn downward slightly so exposing more of the eye ball and facilitating the entry of medicament into the eye. Final location of the device occurs when extension 37 seats on the lower forehead of the user. In this position the second port 35 can be viewed by way of pupil. The head is then thrown back to the position shown in FIG. 8 and while the view from the eye E is directed to the target presented by port 35 the dispenser 38 is squeezed to dispense the requisite amount of medicament. If necessary the head is turned to ensure the gravity acts in a direction ensuring that dispensed material is distributed appropriately over the eye.

THIRD EMBODIMENT

Figure 10:
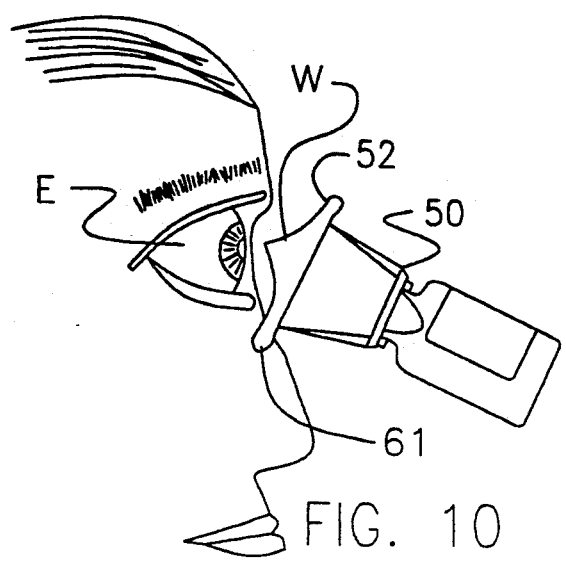
FIGS. 10 and 11 are pictorial views of the device described in connection with FIG. 9.
Figure 11:
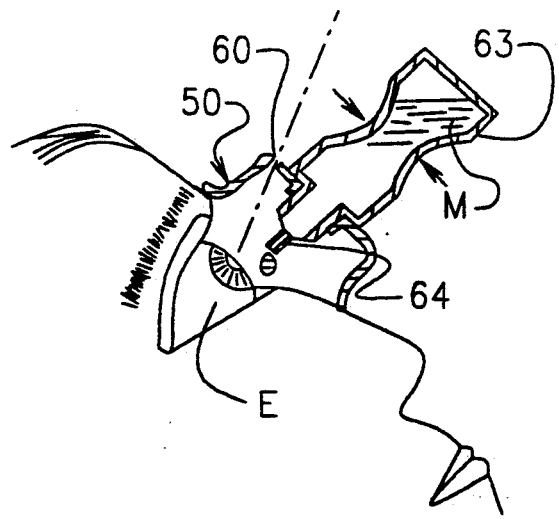

FIGS. 9 to 11

Device 50 comprises a cup 51 of plastic material having a working periphery 52 which, as variously viewed in FIGS. 9 and 10, is of scaphoid shape so as to be able to fit onto the face of a person around an eye. The cup has wing sections W on either side. The cup 51 is made up of a minor first portion 68 and a major second portion 53 which are pivotably connected by way of hinge 54. At the opposite end of first portion 68 to hinge 54 is aperture 55 which with the second portion 52 in its closed position (as indicated in FIG. 10) engages a retaining stud 56 formed in face 57 of second portion 53. The first portion 68 incorporates a crutch 58 which, with the second portion in its closed position, is coaxial with first port 59 in second portion 53. The second portion 53 also contains a second port 60. The cup 51 has an integral lip 61.

Crutch 58 adapted to demountably receive a liquid dispenser 63 (shown detached in FIG. 9 and mounted in FIGS. 10 and 11) containing medicament.M which has a dispensing head 64 which when not in use is closed by a conventional cap 65.

The second port 60 serves as a viewing target so that with device 50 appropriately located to cover the eye E when the eye E is directed to look at the port 60 it is appropriately aligned to receive medicament ejected from dispensing head 64 by squeezing the body of the dispenser 63.

In use prior to locating the device 51 over the eye E the first portion 68 of the cup 51 is hinged outwardly from the second potion 53 to expose the first port 59. The (capped) dispenser 63 is then mounted in crutch 58 by sliding gap 66 between the cap 65 and the shoulders of the dispenser 63 so that the closed dispenser is retained in the crutch 58. The cap 65 is then removed from the dispenser 63 to expose the dispensing head 64. The first portion 68 is then closed to cause aperture 55 to engage retaining stud 56. The relative geometry and alignment of the crutch 58, dispensing head 64, and port 59 are such as to ensure a clear passage for the head between the interior of the cup 51 (as shown in FIG. 10) to the opened position shown in FIG. 9. The assembled device is then moved towards the eye until, as shown in FIG. 10, the lip 61 contacts the top of the cheek below the eye. The device 51 is then moved on towards the eye so that wings W snugly fit around either end of the eye and beneath the eyebrow. In moving into this position the device tends to move downwardly causing the lip 61 to move downwardly along with the lower lid of the eye to be drawn downward slightly so exposing more of the eye ball and facilitating the entry of medicament into the eye. Once the device reaches the position shown in FIG. 11 the head is thrown back. Once the view from the pupil P is directed to the target presented by port 60 the dispenser 63 is squeezed to dispense the requisite amount of medicament M. If necessary the head is turned to ensure that gravity acts in a direction ensuring that dispensed material is distributed appropriately over the eye.

FOURTH EMBODIMENT

FIGS. 12, 13

This embodiment provides for an alternative version of a device according to the present invention comprising a device 81 made up of two shells 82, 83 which are hinged about an integral hinge 84 to enable the shells to be moved between an open position (as shown in FIG. 12) and a closed position (as shown in FIG. 13). In this latter position outer edge 85 of the shell make up a scaphoid shape so as to be able to fit snugly onto the face of a person around an eye. The shells 82, 83 when in their closed position (FIG. 13) serve to retain in port 86 a dispenser for medicament of a type described in connection with the earlier embodiments. A further port 87 provide a viewing target for an eye covered by the device. The shell structure of device 81 provides for a readily assembled device for dispensing eye medicament in a manner that is readily comprehended from the descriptions of the earlier embodiments.

The exemplary embodiments refer to shell components which are generally of opaque material and provided with a target aperture for viewing by the eye. A similar effect can be achieved by making use of a shell of transparent material and a target on the shell based on a shape, colour, mark or a combination of these. Such as arrangement would, for example, enable an observer to check the eye of a user of the device while in use.

I claim:

1. An ophthalmic device, in the form of a cup, consisting of:
   a periphery substantially scaphoid in plan for contacting a facial region in the vicinity of an eye of a user; the cup defining an inner cavity and having a dispensing unit support (14, 34, 58, 86) and a target port (15, 35, 60, 87); the dispensing unit support (14, 34, 58, 86) defining a diameter and being of a sufficiently large size to provide an inlet for a dispensing unit carrying a material to be supplied to the eye and the target port (15, 35, 60, 87) being of a substantially smaller diameter than the dispensing unit support and providing a target for viewing by the eye during use and when the device is being positioned for use, the dispensing unit support and the target port both being provided in a planar base portion of the cup, remote from the periphery, and the dispensing unit support and the target port both being formed solely within said planar base section without extending into the inner cavity defined by the cup.

2. An ophthalmic device as claimed in claim 1 wherein the target port is always completely unobstructed both prior to and during dispensing of the material to be supplied to the eye.

3. An ophthalmic device as claimed in claim 1 wherein the device (10, 30, 50, 81) is fabricated from material which is substantially opaque and the target port (15, 35, 60, 87) is an aperture whereby the eye with which the device is being used can see a distinct target area illuminated from outside the device.

4. An ophthalmic device as claimed in claim 1 wherein the device is fabricated from material which is substantially transparent.

5. An ophthalmic device as claimed in claim 1 wherein a projection (36) is located on the device (30) outside and adjacent the periphery (32) for forming an initial contact point for the device with the facial region in the vicinity of the eye, the projection (36) serving to enhance contact with, and displacement of, a displaceable surface in the facial region with which the projection engages during movement of the device (30) relative to the eye.

6. An ophthalmic device as claimed in claim 1 wherein an aligning member (N) is provided on the device (30) so that as the device (30) is moved towards the eye, the aligning member (N) facilitates positioning by the eye of the device, relative to the eye, at least immediately prior to contact of the device (36) with the facial region of the user.

7. An ophthalmic device in the form of a cup having a periphery substantially scaphoid in plan for contacting a facial region in the vicinity of an eye of a user; the cup defining an inner cavity and having a dispensing unit support (14, 34, 58, 86) and a target port (15, 35, 60, 87); the dispensing unit support (14, 34, 58, 86) defining a diameter and being of a sufficient large size to provide an inlet for a dispensing unit carrying a material to be supplied to the eye and the target port (15, 35, 60, 87) being of a substantially smaller diameter than the dispensing unit support and providing a target for viewing by the eye during use and when the device is being positioned for use, the dispensing unit support and the target port both being provided in a planar base portion of the cup, remote from the periphery, and the dispensing unit support and the target port both being formed solely within said planar base portion without extending into the inner cavity defined by the cup;

wherein the cup has a pair of opposed wing sections which engage the facial region of a user adjacent the nose and the ear of the eye being treated.

8. An ophthalmic device in the form of a cup having a periphery substantially scaphoid in plan for contacting a facial region in the vicinity of an eye of a user; the cup defining an inner cavity and having a dispensing unit support (14, 34, 58, 86) and a target port (15, 35, 60, 87); the dispensing unit support (14, 34, 58, 86) defining a diameter and being of a sufficient large size to provide an inlet for a dispensing unit carrying a material to be supplied to the eye and the target port (15, 35, 60, 87) being of a substantially smaller diameter than the dispensing unit support and providing a target for viewing by the eye during use and when the device is being positioned for use, the dispensing unit support and the target port both being provided in a planar base portion of the cup, remote from the periphery, and the dispensing unit support and the target port both being formed solely within said planar base portion without extending into the inner cavity defined by the cup;

wherein the device is provided with a lip for contacting the facial region below the eye of the user and an opposed extension for engaging a forehead portion of the user, the lip facilitating a downward movement of a lower eyelid of a user, once engaged therewith, thereby to expose more of the eye and facilitate entry of the material to be supplied to the eye.

* * * * *